United States Patent
Kraemer

(10) Patent No.: US 7,704,213 B2
(45) Date of Patent: Apr. 27, 2010

(54) METHOD AND DEVICE FOR DETERMINING THE BLOOD FLOW IN A BLOOD-CONDUCTING TUBE

(75) Inventor: Matthias Kraemer, Friedrichsdorf (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1346 days.

(21) Appl. No.: 10/540,110

(22) PCT Filed: Dec. 4, 2003

(86) PCT No.: PCT/EP03/13730

§ 371 (c)(1),
(2), (4) Date: Jun. 20, 2005

(87) PCT Pub. No.: WO2004/057279

PCT Pub. Date: Jul. 8, 2004

(65) Prior Publication Data

US 2006/0064025 A1     Mar. 23, 2006

(30) Foreign Application Priority Data

Dec. 19, 2002 (DE) ................................ 102 59 437

(51) Int. Cl.
*A61B 5/026* (2006.01)
(52) U.S. Cl. ..................... 600/504; 600/505; 600/507; 204/646; 204/739; 204/742; 604/4.01; 604/5.01; 604/6.06; 604/6.09; 604/6.16; 604/8
(58) Field of Classification Search ................ 604/5.01, 604/8, 6.06, 6.09, 6.16; 210/646, 739, 742; 600/504, 505, 507
See application file for complete search history.

(56) References Cited

U.S. PATENT DOCUMENTS 3,446,073 A     5/1969    Auphan et al.

(Continued)

FOREIGN PATENT DOCUMENTS

DE     195 28 907 C1     11/1996

(Continued)

OTHER PUBLICATIONS

Kaye, M., et al., "A New Technique for Measuring Blood Flow in Polytetrafluorethylene Grafts for Hemodialysis", Clinic of Nephrology, vol. 8 No. 6, May 1977, pp. 533-534.
Weitzel, W.F., et al., "Analysis of Variable Flow Doppler Hemodialysis Access Flow Measurements and Comparison with Ultrasound Dilution", Amer. Journal of Kidney Diseases, vol. 38, No. 5, Nov. 2001, pp. 935-940.

*Primary Examiner*—Robert L Nasser
*Assistant Examiner*—Michael D'Angelo
(74) *Attorney, Agent, or Firm*—Jacobson Holman PLLC

(57) ABSTRACT

A measurement method for determining the blood flow rate $Q_F$ in blood carrying lines is provided. It may be used in particular to determine the blood flow in a patient's vessel, which is connected to the extracorporeal circulation of a blood treatment machine by an arterial line and a venous line. According to the method, the net rate dX/dt of a variable X is determined, with X being derived from a physicochemical variable Y of the blood with the help of values $Y_A$ and $Y_V$ which are adequately constant over time and which respectively characterize the physicochemical property in the arterial line and the venous line during the measurement interval. The net rate dX/dt is then used to determine the blood flow rate $Q_F$. The targeted use of indicators is not necessary.

24 Claims, 2 Drawing Sheets

U.S. PATENT DOCUMENTS

| | | | |
|---|---|---|---|
| 4,894,164 A * | 1/1990 | Polaschegg | 210/646 |
| 5,685,989 A * | 11/1997 | Krivitski et al. | 210/646 |
| 5,830,365 A | 11/1998 | Schneditz | |
| 5,866,015 A | 2/1999 | Krämer | |
| 6,189,388 B1 | 2/2001 | Cole et al. | |
| 6,827,698 B1 | 12/2004 | Kleinekofort | |
| 7,097,630 B2 | 8/2006 | Gotch et al. | |

FOREIGN PATENT DOCUMENTS

| | | |
|---|---|---|
| DE | 199 17 197 C1 | 7/2000 |
| DE | 199 17 196 A1 | 10/2000 |
| EP | 0 781 161 | 7/1997 |
| EP | 0 928 614 A1 | 7/1999 |
| EP | 928614 A1 * | 7/1999 |
| JP | 9 173444 | 7/1997 |
| JP | 11 262520 | 9/1999 |
| JP | 2000 325471 | 11/2000 |
| WO | WO 96/08305 A1 | 3/1996 |
| WO | WO 98/17193 | 4/1998 |
| WO | WO 00/24440 | 5/2000 |
| WO | WO 01/28419 A2 | 4/2001 |
| WO | WO 02/053212 A1 | 7/2002 |

* cited by examiner

METHOD AND DEVICE FOR DETERMINING THE BLOOD FLOW IN A BLOOD-CONDUCTING TUBE

This is a nationalization of PCT/EP03/013730 filed Dec. 4, 2003 and published in German.

BACKGROUND OF THE INVENTION

1. Field of the Invention

This invention relates to the field of measurement methods for determining the blood flow in a line carrying blood.

2. Description of the Related Art

In patients with renal failure, hemodialysis treatment is one possibility for replacing insufficient kidney. In hemodialysis, blood is withdrawn from the patient through an arterial blood line, purified in a blood treatment element and returned to the patient through a venous blood line. The blood treatment element may be designed as a hemodialyzer, in which blood passes through a first of two chambers separated from by a semipermeable membrane, while dialysis fluid flows through the second chamber. Fluid can be withdrawn from the blood by controlling the pressure ratios in the dialyzer.

It is also possible for the blood treatment element to be designed as a hemofilter. In this case, fluid is only removed from the blood through the membrane, but no fluid passes continuously through the second chamber. Most of the fluid volume withdrawn is returned to the patient by administering replacement fluids.

Such treatment methods require an adequate blood flow of approximately 200 to 450 ml/min to achieve adequate purification of the blood within the treatment, which lasts several hours and is performed approximately three times a week. For this reason, dialysis-dependent patients generally have an arterial-venous fistula or a shunt installed between an artery and a vein. Adequate blood flow develops in this vessel, while at the same time the vessel assumes enlarged dimensions in comparison with the other blood vessels, which is advantageous for puncture with a needle.

The blood flow in such a vessel may vary over time. In particular, a gradual blockage of the vessel may occur due to stenosis. If the blood flow drops below the required blood flow rate in the extracorporeal circulation, the blood purification capacity of the treatment is impaired. In most cases, the vascular stenosis is already so advanced in such a case that it can be corrected only by a procedure such as surgery. Therefore, it would be desirable to learn of such an imminent complication at an earlier point in time, so that other techniques would also be available for eliminating this complication.

A number of techniques have been proposed for measuring the blood flow in a vessel. Methods such as ultrasonic Doppler systems, used independently or with an extracorporeal blood circulation (e.g., Weitzel et al., Am. J. Kidney Dis. 38, 935 (2001)), require additional equipment and handling is complicated. In addition, the measurements must be performed by specially trained personnel.

With another known method, an indicator is infused into a vessel at a constant infusion rate, and samples are taken from the vessel downstream (Kaye et al., Clinical Nephrology 8, 533 (1977)). The fistula flow is deduced from the analysis of the dilution values. This method requires an additional infusion device and a sampling device as well as controlled use of an indicator.

Other systems use the extracorporeal blood circulation of the hemodialysis machine to measure the fistula flow. U.S. Pat. No. 5,866,015 describes a method in which the blood flow rate in the extracorporeal circulation is varied, and the changes in blood temperature in the extracorporeal circulation are measured and analyzed. German Patent 199 17 197 C1 also describes the use of various blood flow rates to then analyze the pattern of the measured pressures in the extracorporeal circulation. One disadvantage of these methods is that controlling different blood flow rates is a complicated process and has a negative effect on the blood treatment. In addition, in the method proposed in German Patent 199 17 197 C1, the fistula flow must also be interrupted for a portion of the measurement.

According to the teaching of European Patent 781 161 B1, in addition to exchanging the accesses on the fistula, it is necessary to vary a physical property of the blood at the outlet end of the extracorporeal blood circulation to generate a blood feature that can be differentiated. The extent of this change is then analyzed in the sense of a dilution curve. This method also requires additional intervention procedures such as injection of an indicator solution or another targeted change in the blood. The analysis involves detection of the entire chronological course of the changes, which must be integrated over the bolus-type changes.

Other methods such as those described in International Patents WO 02/053212 A1 or WO 98/17193 A1 also have in common the fact that it is necessary to detect a targeted change in the extracorporeal blood as well as the variations therein over time.

In addition to describing the determination of cardiopulmonary recirculation, U.S. Pat. No. 5,830,365 describes one possibility for determining the fistula flow with the help of recirculation measurements, but bolus-like changes in blood properties are also induced in a targeted manner and analyzed here for this recirculation measurement.

U.S. Pat. No. 4,894,164 describes a method and a device for measuring and influencing the heat balance of a patient during an extracorporeal blood treatment. A determination of the fistula flow is not provided.

SUMMARY OF THE INVENTION

Therefore, the object of this invention is to provide a method and a device for determining blood flow in a line carrying blood, such that this method can be used even without additional targeted effects, i.e., controlled effects on the properties of the blood.

According to the teaching of this invention, this object is achieved by a method of determining a blood flow rate $Q_F$ in a blood-carrying line that is coupled to an extracorporeal blood treatment device through an arterial line and a venous line. A portion of blood in the blood-carrying line is branched off at a first location through the arterial line and is returned to the blood-carrying line at a second location through the venous line such that this portion of blood passes from the arterial line to the extracorporeal blood treatment device and then to the venous line. The method includes the steps of determining a physicochemical variable Y of the blood, which is constant over a period of time for a measurement interval, in the arterial line upstream of the extracorporeal blood treatment device as having value $Y_A$ and in the venous line downstream of the extracorporeal blood treatment device as having value $Y_V$; determining a net rate dX/dt of a variable X derived from the physicochemical variable Y into or out of the blood-carrying line during the measurement interval from the values $Y_A$ and $Y_V$ as a difference between rate $dX_A/dt$ as measured in blood removed from the blood-carrying line through the arterial line and rate $dX_V/dt$ as measured in blood supplied back to the blood-carrying line through the venous line; and using the net rate dX/dt to determine the blood flow rate $Q_F$ in the blood-carrying line.

The invention also includes a device for measuring the blood flow in a blood-carrying line, the device comprising an arterial line branching off from the blood-carrying line through which blood is removed from the blood-carrying line; a venous line opening into the blood-carrying line through which blood is supplied to the blood-carrying line; arterial measurement means and venous measurement means for determining a physicochemical variable Y of the blood in the arterial line with the value $Y_A$ and in the venous line with the value $Y_V$, these variables being constant over a period of time for a measurement interval; and an analyzer unit connected to the arterial measurement means and the venous measurement means which is configured to determine a net rate dX/dt of a variable X derived from the physicochemical variable Y into or from the blood-carrying line during the measurement interval as the difference between a rate $dX_A/dt$ as measured in blood removed from the blood-carrying line through the arterial line and a rate $dX_V/dt$ as measured in blood supplied back to the blood-carrying line through the venous line from the values $Y_A$ and $Y_V$, the analyzer unit also being configured to use the net rate dX/dt to determine the blood flow rate $Q_F$ in the blood-carrying line.

This invention may be used in particular to determine the blood flow in a patient's blood vessel. Use of this invention is recommended in particular whenever corresponding blood lines are used anyway as part of an extracorporeal blood treatment. The analysis according to this invention may then be implemented essentially by specification of the software, by using components already on hand.

This invention may be used in general with lines that carry blood, even when they run outside the human body—e.g., also including in-vitro applications.

BRIEF DESCRIPTION OF THE DRAWINGS

Additional details and advantages of this invention are described in greater detail on the basis of an exemplary embodiment of the device according to this invention, as illustrated in the drawings, which show.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
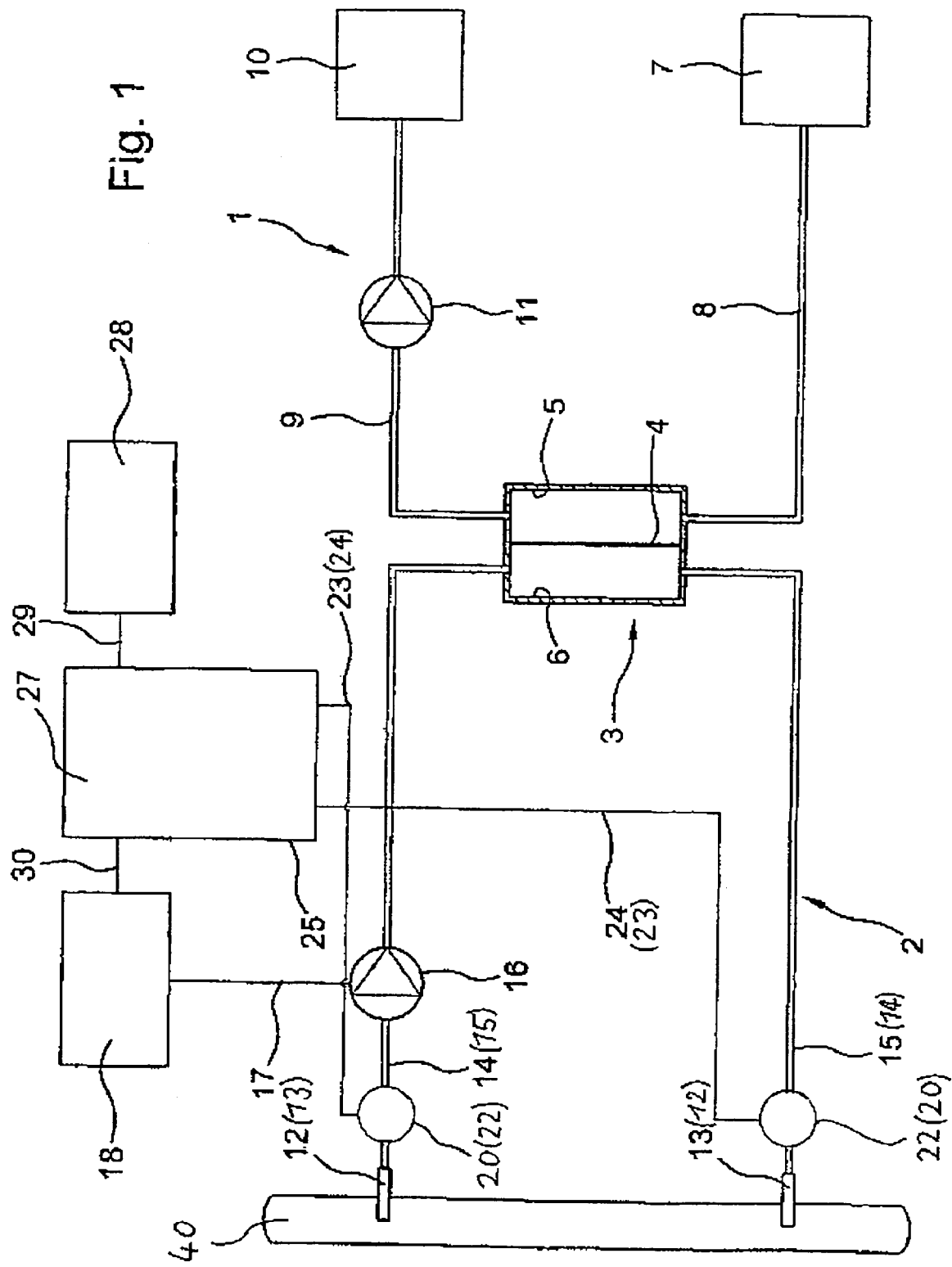
FIG. 1 a schematic diagram of an embodiment of the device according to this invention and FIG. 2 various constellations of cases for blood flow in the blood-carrying line whose flow rate $Q_F$ is to be determined.

The embodiment of the device according to this invention as illustrated in FIG. 1 includes a dialysis circulation 1 and a blood circulation 2. Dialysis fluid is conveyed in dialysis circuit 1 by means of a delivery device 11 from a dialysis fluid source 7 to an outlet 10 through a dialysis fluid inlet line 8, the dialysis fluid chamber 5 of a dialyzer 3 and through the dialysis fluid outlet line 9.

Blood is taken from a blood-carrying line 40 in blood circulation 2 at a first location through an arterial access 12. An arterial line 14 to which is connected an arterial temperature sensor 20 and to which a blood pump 16 is also connected is connected to this access. Arterial line 14 leads into the blood chamber 6 of the dialyzer 3. From this chamber, blood is returned via a venous line 15 and a venous access 13 to the blood-carrying line 40 at a second location. A venous temperature sensor 22 is connected to the venous line 15.

The blood chamber 3 and the dialysis fluid chamber 5 are separated by a semipermeable membrane 4.

This device also has an analyzer unit 27, which is connected to the arterial sensor 20 and to the venous sensor 22 for detecting the respective temperatures via measurement lines 23 and 24. The analyzer unit 27 is also connected by a line 30 to a control unit 18 for triggering the blood pump 16 via a line 17. A delivery rate may be set for the blood pump 16 via the control unit 18, and at the same time this delivery rate is also transmitted to the analyzer unit 27 over the line 30. The analyzer unit 27 is connected to a display device 28 by a line 29, so that the measured data and control data as well as the analytical results may be displayed on this display device.

This invention is based on the observation that it is not necessary to perform any specific manipulation of the blood properties, e.g., in venous line 15, in order to determine the line flow rate $Q_F$ in line 40. Instead, it is sufficient to determine the net rate dX/dt of a variable X, which is derived from the physicochemical quantity Y of the blood, where this net rate refers to the amount of blood removed from the line 40 over the arterial line 14 and supplied over the venous line 15. The net rate dX/dt, which is determined from the difference between the arterial rate $dX_A/dt$ and the venous rate $dX_V/dt$, can be calculated for the case of sufficient time constancy during a measurement interval with the help of the values $Y_A$ and $Y_V$ of the physicochemical property Y in the arterial and venous lines. The net rate dX/dt can then be used to derive the line flow rate $Q_F$.

In this situation, the following equation holds for the net rate dX/dt:

$$\frac{dX}{dt} = \frac{dX_V}{dt} - \frac{dX_A}{dt} = Q_B(Y_V - Y_A), \tag{1}$$

where $Q_B$ is the blood flow rate in the arterial line or the venous line.

Figure 2:
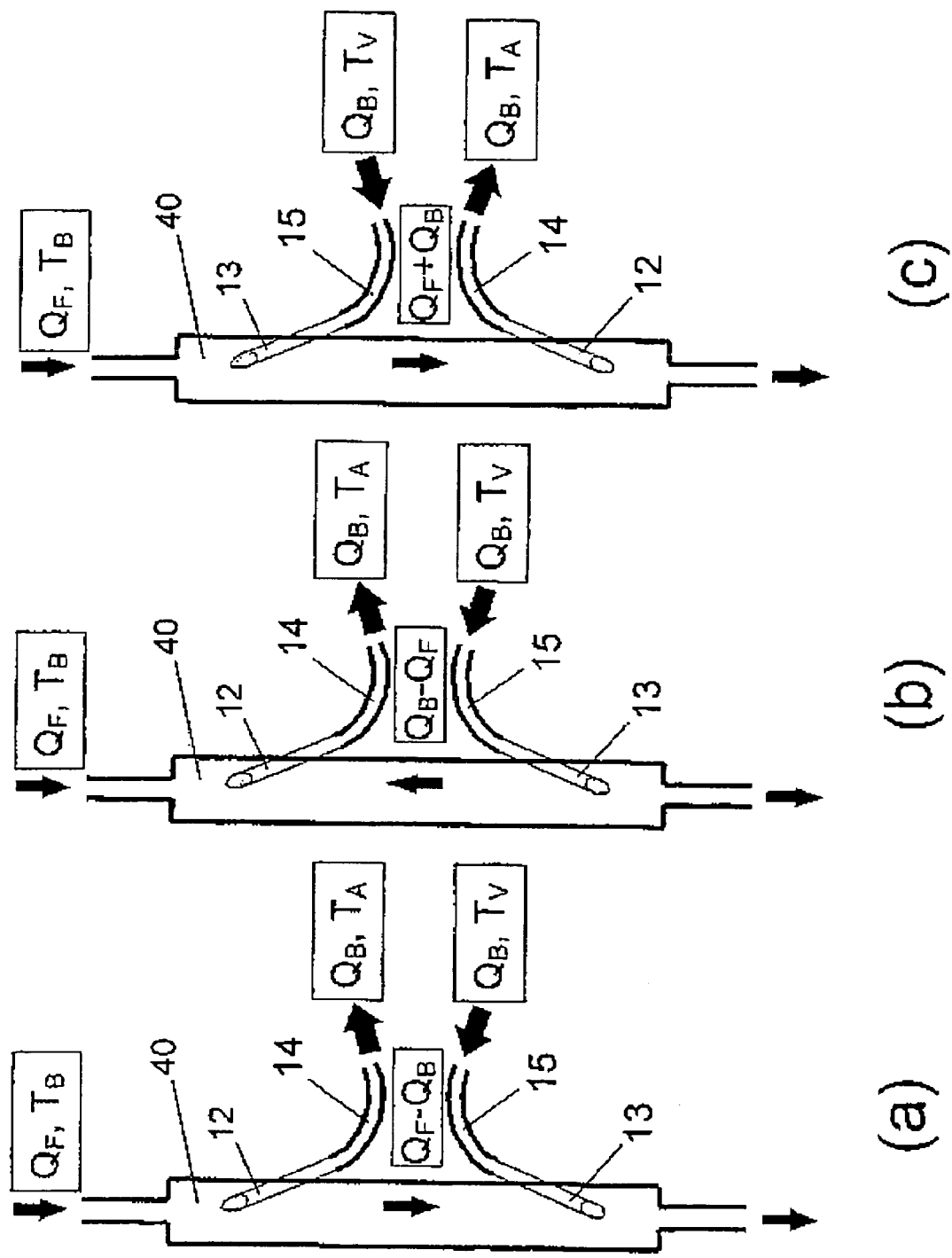

For the blood flow rate $Q_F$ to be determined and the blood flow rate $Q_B$ in blood circulation 2, various case are possible, as illustrated in detail in FIG. 2. In FIGS. 2a and 2b, branch 12 of the arterial line 14 is situated upstream from branch 13 of the venous line 15. FIG. 2a concerns the case when the blood flow rate $Q_B$ is less than the blood flow rate $Q_F$ to be measured. In this case, there remains a flow rate $Q_F-Q_B$ between the arterial branch and the venous branch, and there is no direct recirculation in line 40 of blood returned through the venous line 15 to the arterial line 14. In this case, the present invention is not applicable initially.

However, if a blood flow rate $Q_B$, which exceeds blood flow rate $Q_F$, is stipulated (FIG. 2b), then there is recirculation in the blood-carrying line 40. This situation may be induced in a controlled manner in those cases when the blood flow rate $Q_F$ to be measured is expected only in a certain value range. This value range may then be exceeded by $Q_B$, so that recirculation is induced. In this case, the blood flow rate $Q_B$ is composed of two components:

$$Q_B = R \cdot Q_B + Q_F \tag{2}$$

The first component concerns the recirculating part and the second component concerns the part flowing into line 40. The recirculation factor R indicates the percentage of recirculation flow in the blood flow rate $Q_B$.

The recirculation component, however, does not make any contribution to the net rate dX/dt, because this component is added to and removed from blood-carrying line 40 equally. Only the second part can make a contribution to this net rate dX/dt:

$$\frac{dX}{dt} = Q_F(Y_V - Y_B), \quad (3)$$

where $Y_B$ is the physicochemical property in the line 40 upstream from the first branch 12. After solving for $Q_F$, equation (3) yields:

$$Q_F = \frac{\frac{dX}{dt}}{Y_V - Y_B} = \frac{Q_B(Y_V - Y_A)}{Y_V - Y_B}. \quad (4)$$

If Y is the thermal energy per unit of volume of blood, and X is the thermal energy E of the blood in the blood-carrying line 40, then equation (4) yields:

$$Q_F = \frac{\frac{dE}{dt}}{c_E \rho_B (T_V - T_B)} = \frac{Q_B(T_V - T_A)}{(T_V - T_B)}, \quad (5a)$$

where $T_A$, $T_V$ and $T_B$ stand for the temperatures of the blood in the arterial line 20, the venous line 22 and in the blood flowing into blood-carrying line 40. The thermal capacity of the blood is given as $c_E$ and the density of the blood is given as $\rho_B$, where it is assumed that these are the same in all lines.

If Y is the concentration c of the substance, and X is the quantity C of this substance in blood-carrying line 40, then equation (5a) would be rewritten as equation (5b) with corresponding indices:

$$Q_F = \frac{\frac{dC}{dt}}{(c_V - c_B)} = \frac{Q_B(c_V - c_A)}{(c_V - c_B)}. \quad (5b)$$

The method according to this invention can be implemented as follows by the embodiment in FIG. 1, which shows a hemodialysis device, also known as a dialysis machine. It has been found that during an interval of a few seconds to a few minutes in a dialysis treatment, the temperature of the blood in the lines 14, 15 and 40 may be assumed to remain sufficiently constant. The analyzer device 27 stores the temperatures $T_A$ determined during the measurement time interval with the sensors 20 and 22 in the arterial line 14 and the temperatures $T_V$ in the venous line 15. To increase the accuracy, the sensors 20 and 22 are placed as close as possible to the branches 12 and 13, respectively. On the basis of the distance traveled by the blood from the arterial sensor 20 to the venous sensor 22—in particular by way of the dialyzer 3—it has surprisingly been found that the temperatures $T_A$ and $T_V$ in the application case are almost always sufficiently different inherently to permit a measurement.

The blood flow value $Q_B$ is reported by the control unit 18 to the analyzer unit. This blood flow value has been selected by the control unit 18 to be sufficiently high, so that the case according to FIG. 2b will occur.

In order for the analyzer unit 27 to now be able to determine the blood flow rate $Q_F$ in the blood-carrying line 40 with the help of equation (5a), the following additional measure is taken in this embodiment: immediately before or after the measurement of the temperatures $T_A$ and $T_V$, the control unit sets the blood flow rate at a value such that $Q_{B2} < Q_{B1}$ for the case illustrated in FIG. 2a. In dialysis, a value of $Q_{B2}=150$ ml/min, for example, would be suitable. Then the analyzer unit 27 detects the temperature value $T_A$ for the blood flow rate $Q_{B2}$. This value, which is also stored by the analyzer unit 27, corresponds to the temperature $T_B$ in equation (5a). Thus, all the variables in equation (5a) are known, and the analyzer unit 27 can determine the blood flow rate $Q_F$. Optionally, this value is then displayed on the display device 28.

Another variant of an embodiment of this invention is based on the situation illustrated in FIG. 2c. In this case, the arterial line 14 branches off from the blood-carrying line 40 downstream from the venous line 15. This constellation is indicated in parentheses in FIG. 1. In the case of the device according to FIG. 1, this may be accomplished easily by reversing the direction of flow of the blood pump 16. It would equally be possible to exchange the connections 12 and 13. In this regard, reference is made explicitly to the disclosure content of German Patent 195 28 907 C1, which discloses a shunt circuit for this case. This circuit can be triggered manually or automatically by the control unit 18.

By analogy with equation (2), the following holds for the case according to FIG. 2c:

$$Q_B = R \cdot Q_B + (1-R)Q_B \quad (6).$$

In this case it also holds that $$R = \frac{Q_B}{Q_B + Q_F}. \quad (7)$$

Again only the non-recirculating second component in equation (6) makes a contribution to the net rate dX/dt, which is to be designated as $dX_{rec}/dt$ for the case according to FIG. 2c.

Equation (3) is thus rewritten as follows:

$$\frac{dX_{rec}}{dt} = \frac{dX_{V,rec}}{dt} - \frac{dX_{A,rec}}{dt} = \left(1 - \frac{Q_B}{Q_B + Q_F}\right) Q_B(Y_{V,rec} - Y_B). \quad (8)$$

When solved for $Q_F$, equation (8) yields:

$$Q_F = \frac{Q_B \frac{dX_{rec}}{dt}}{Q_B(Y_{V,rec} - Y_B) - \frac{dX_{rec}}{dt}} = \frac{Q_B(Y_{V,rec} - Y_{A,rec})}{Y_{A,rec} - Y_B}. \quad (9)$$

It is now possible to proceed in a manner similar to that used for the case according to FIG. 2b. Measured variable $Y_B$ may also be determined in a similar manner, in which case the connections must be made as shown in FIG. 2a. This can be performed manually or it can be controlled by the control unit 18, by reversing the direction of output of blood pump 16 or by using a suitable shunt circuit. The relationships similar to equations (5a) and (5b) are derived by inserting the following as variables into equation (9): the temperature T (which is yet to be multiplied by the specific thermal capacity $c_E$ and the density $\rho_B$) and/or the concentration c.

In a third variant of the embodiment of this invention, which is especially preferred, a first measurement is performed initially in the constellation according to FIG. 2a or FIG. 2b for the net rate dX/dt. Then by reversing the direction of delivery of the blood pump 16 or by using a corresponding shunt circuit, a second measurement of the net rate $dX_{rec}/dt$ is performed in the constellation according to FIG. 2c. Then, dividing equation (8) by equation (1) yields equation (10):

$$\frac{\frac{dX_{rec}}{dt}}{\frac{dX}{dt}} = \frac{Q_F}{Q_B + Q_F} \frac{Y_{V,rec} - Y_B}{Y_V - Y_A}. \tag{10}$$

If the blood flow rate $Q_B$ is selected to be so low that the case according to FIG. 2a for the measurement of dX/dt prevails, then $Y_A = Y_B$. When inserted into equation (10), this yields the following for this case:

$$Q_F = \frac{Z}{1-Z} Q_B, \tag{11a}$$

where $$Z = \frac{\frac{dX_{rec}}{dt}}{\frac{dX}{dt}} \frac{Y_V - Y_A}{Y_{V,rec} - Y_A} = \frac{Y_{V,rec} \; A,rec}{Y_{V,rec} - Y_A}. \tag{11b}$$

In this variant, the analyzer unit 27 calculates the blood flow rate $Q_F$ according to equations (11a) and (11b), to which end the analyzer unit 27 initially stores the individual measured values as in the preceding variants.

The relationships similar to those in equations (5a) and (5b) are now derived again by inserting the following variables: the temperature T (which is yet to be multiplied by the specific thermal capacity $c_E$ and the density $\rho_B$) and/or the concentration c into equation (11b). If the measurements for dX/dt and $dX_{rec}/dt$ are to be performed at different blood flow rates $Q_B$ and $Q_{B,rec}$, then equation (11) can be adapted accordingly.

Equation system (11a) and (11b) can now be further simplified under certain conditions. In the case of the device illustrated in FIG. 1, blood flows through the blood chamber 6 of the dialyzer 3, during which process there is a mass exchange and an exchange of energy with the dialysis fluid in the dialysis fluid chamber 5. The two fluids flow through the dialyzer in countercurrent—as is generally the practice in hemodialysis—and the dialysis fluid flow rate is generally set higher than the blood flow rate. Depending on the prevailing flow ratios and the specific dialyzers used, and the temperature in particular, the situation often occurs that the blood at the outlet of the blood chamber 6 assumes the temperature of the dialysis fluid at the entrance to the dialysis fluid chamber 5.

Then, if the temperature in dialysis fluid delivery line 8 is kept constant during the measurement phase, which lasts from a few seconds to a few minutes at most, then the temperature of the blood in the venous line 15 also remains constant. Minor deviations in the temperature of the blood in the arterial line 14 do not have any effect. This means that the temperatures $T_V$ and $T_{V,rec}$ in equation (11b) are identical. (For the embodiment shown in FIG. 1, the dialysis flow must be reversed here for the determination of $dX_{rec}/dt$. This is not necessary when using a shunt circuit in which the flow conditions are maintained in the dialyzer 3.) Thus, the numerator and the denominator of the second fraction after the first equal symbol are decreased by identical amounts. When inserted in equation (11a), this yields equation (12):

$$Q_F = Q_B \frac{\frac{dX_{rec}}{dt}}{\frac{dX}{dt} - \frac{dX_{rec}}{dt}}. \tag{12}$$

The net rates dX/dt and $dX_{rec}/dt$ determined according to equation (1) can be used especially easily in this case to determine the blood flow rate in the blood-carrying line 40. This is always the case when the criterion $Y_V = Y_{V,rec}$ is met.

The embodiments described here are derived under the assumption that the blood flow rate in the arterial line 14 is identical to that in the venous line 15.

In hemodialysis, there may be minor deviations from this assumption in certain cases when fluid is removed from the arterial and/or venous lines by ultrafiltration. However, it is within the technical capabilities of those skilled in the art to adapt the equations to conform to this situation. In addition to the blood flow rate in one of the lines, it is necessary then to determine only the ultrafiltration flow rate as an additional value.

The same thing is also true in the case of a measurement on a patient's vessels for so-called cardiopulmonary recirculation. In cardiopulmonary recirculation, blood delivered from the venous line 15 to line 40 with the properties $Y_V$ reaches the arterial line 14, where it is recirculated directly through the patient's bloodstream without undergoing sufficient metabolic or temperature balancing in other body areas. However, this component is generally relatively small.

This invention makes available a simple method and a corresponding device with which it is possible to determine with minimal effort the blood flow rate in a line from which an arterial line and a venous line branch off. These measurements can be performed within a short period of time, so that the effect on a concomitant blood treatment, if any, can be minimized or negligible. Targeted addition of indicators is not necessary.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A method of determining a blood flow rate $Q_F$ in a blood-carrying line that is coupled to an extracorporeal blood treatment device through an arterial line and a venous line using a processing unit, a portion of blood in said blood-carrying line being branched off at a first location through said arterial line and being returned to said blood-carrying line at a second location through said venous line such that said portion of blood passes from said arterial line to said extracorporeal blood treatment device and then to said venous line, the method comprising the steps of: determining, using a measurement means a physicochemical variable Y of the blood, which is constant over a period of time for a measurement interval, in the arterial line upstream of said extracorporeal blood treatment device as having the value $Y_A$ and in the venous line downstream of said extracorporeal blood treatment device as having value $Y_V$, determining, using said processing unit a net rate $dX/dt$ of a variable X derived from the physicochemical variable Y into or out of the blood-carrying line during the measurement interval from the values $Y_A$ and $Y_V$ as a difference between rate $dX_A/dt$ as measured in blood removed from the blood-carrying line through the arterial line and the rate $dX_V/dt$ as measured in blood supplied back to the blood-carrying line through the venous line and using the net rate $dX/dt$ to determine the blood flow rate $Q_F$ in said blood-carrying line using said processing unit.

2. The method according to claim 1, wherein a blood flow rate $Q_B$ is determined in the arterial line and in the venous line for the determination of the rate removed $dX_A/dt$ and the rate supplied $dX_V/dt$.

3. The method according to claim 2, wherein the physicochemical variable Y is the thermal energy per unit of volume of blood, and the variable X, which is derived from Y, denotes the thermal energy E of the blood in the blood-carrying line.

4. The method according to claim 3, wherein a temperature $T_A$ in the arterial line and a temperature $T_V$ in the venous line are determined for the determination of the net thermal energy rate $dE/dT$, and the net energy rate is determined on the basis of the equation $$\frac{dE}{dt} = \frac{dE_V}{dt} - \frac{dE_A}{dt} = c_E \rho_B Q_B (T_V - T_A)$$

where $c_E$ is the specific thermal capacity and $\rho_B$ is the density of the blood.

5. The method according to claim 2, wherein the physicochemical variable Y is a concentration c of a substance in blood, and X is a quantity C of the substance in the blood-carrying line.

6. The method according to claim 5, wherein the concentrations $c_A$ of the substance in the arterial line and $c_V$ in the venous line are determined for the determination of a net substance quantity rate $dC/dt$, and the net substance quantity rate is determined according to the equation:

$$\frac{dC}{dt} = \frac{dC_V}{dt} - \frac{dC_A}{dt} = Q_B(c_V - c_A)$$

7. The method according to claim 1, wherein the arterial line branches off from the blood-carrying line upstream from the venous line, and the blood flow rate $Q_F$ is determined on the basis of the $$Q_F = \frac{\frac{dX}{dt}}{Y_V - Y_B}$$

where $Y_B$ is the physicochemical variable in the blood-carrying line upstream from a branch in the arterial line.

8. The method according to claim 2, wherein the arterial line branches off from the blood-carrying line downstream from the venous line, where the net rate is designated as $dX_{rec}/dt$, and the physicochemical variable in the venous line is designated as $Y_{V,rec}$, and the blood flow rate $Q_F$ is determined on the basis of the equation:

$$Q_F = \frac{Q_B \frac{dX_{rec}}{dt}}{Q_B(Y_{V,rec} - Y_B) - \frac{dX_{rec}}{dt}}$$

where $X_B$ is the physicochemical variable in the blood-carrying line upstream from a branch in the venous line.

9. The method according to claim 2, wherein both the net rate $dX/dt$ with the upstream branch in the arterial line relative to the venous line from the blood-carrying line as well as the net rate $dX_{rec}/dt$ with a downstream branch in the arterial line relative to the venous line from the blood-carrying line are determined at the same blood flow rate $Q_F$ and the blood flow rate $Q_F$ is determined according to the following equation:

$$Q_F = \frac{Z}{1-Z} Q_B \text{ where } Z = \frac{\frac{dX_{rec}}{dt}}{\frac{dX}{dt}} \frac{Y_V - Y_A}{Y_{V,rec} - Y_A}.$$

10. A device for measuring blood flow in a blood-carrying line, comprising:

an arterial line branching off from the blood-carrying line through which blood is removed from the blood-carrying line;

a venous line opening into the blood-carrying line through which blood is supplied to the blood-carrying line;

arterial measurement means and venous measurement means for determining a physicochemical variable Y of the blood in the arterial line with the value $Y_A$ and in the venous line with the value $Y_V$, these variables being constant over a period of time for a measurement interval;

an analyzer unit connected to the arterial measurement means and the venous measurement means, said analyzer unit being configured to determine a net rate $dX/dt$ of a variable X derived from the physicochemical variable Y into or from the blood-carrying line during the measurement interval as the difference between a rate $dX_A/dt$ as measured in blood removed from the blood-carrying line through the arterial line and a rate $dX_V/dt$ as measured in blood supplied back to the blood-carrying line through the venous line from the values $Y_A$ and $Y_V$, said analyzer unit being further configured to use the net rate $dX/dt$ to determine the blood flow rate $Q_F$ in said blood-carrying line.

11. The device according to claim 10, wherein means are provided for detecting and/or adjusting a blood flow rate $Q_F$ in the arterial line and in the venous line.

12. The device according to claim 11, wherein the means for detecting the blood flow rate $Q_B$ includes a flow sensor, which is connected to the analyzer unit.

13. The device according to claim 12, wherein the means for detecting the blood flow rate $Q_B$ includes a control unit which is used for setting a delivery rate of a blood pump, which is situated in the arterial line and/or the venous line and is connected to the analyzer unit.

14. The device according to claim 11, wherein the physicochemical variable Y denotes a thermal energy per unit of volume of blood, and the variable X derived therefrom denotes a thermal energy E of the blood in the blood-carrying line.

15. The device according to claim 14, wherein the measurement means includes a temperature sensor ($T_A$) in the arterial line and a temperature sensor ($T_V$) in the venous line for determining the net thermal energy rate dE/dt, and the analyzer unit is configured to determine the net thermal energy rate by using the equation:

$$\frac{dE}{dt} = \frac{dE_V}{dt} - \frac{dE_A}{dt} = c_E \rho_B Q_B (T_V - T_A)$$

where $c_E$ is the specific thermal capacity, and $\rho_B$ is the density of blood.

16. The device according to claim 11, wherein the physicochemical variable is a concentration c of a substance in the blood, and X is a quantity C of said substance in the blood-carrying line.

17. The device according to claim 16, wherein to determine the net substance quantity dC/dt, the measurement means includes a concentration sensor ($c_A$) in the arterial line and a concentration sensor ($c_V$) in the venous line, and the analyzer unit is suitable for determining the net substance quantity rate on the basis of the equation:

$$\frac{dC}{dt} = \frac{dC_V}{dt} - \frac{dC_A}{dt} = Q_B (c_V - c_A).$$

18. The device according to claim 10, wherein the arterial line branches off from the blood-carrying line upstream from the venous line, and the analyzer unit is configured to perform a determination of the blood flow rate $Q_F$ on the basis of the equation:

$$Q_F = \frac{\frac{dX}{dt}}{Y_V - Y_B}$$

where $Y_B$ is the physicochemical variable in the blood-carrying line upstream from the branch the arterial line.

19. The device according to claim 11, wherein the arterial line branches off from the blood-carrying line upstream from the venous line, whereby the net rate is designated as $dX_{rec}/dt$ and the physicochemical variable in the venous line is designated as $Y_{V,rec}$, and the analyzer unit is configured to perform a determination of the blood flow rate $Q_F$ by using the equation:

$$Q_F = \frac{Q_B \frac{dX_{rec}}{dt}}{Q_B(Y_{V,rec} - Y_B) - \frac{dX_{rec}}{dt}}$$

where $Y_B$ is the physicochemical variable in the blood-carrying line upstream from a branch in the venous line.

20. The device according to claim 11, wherein the analyzer unit is configured to determine both the net rate dX/dt with an upstream branch in the arterial line with respect to the venous line from the blood-carrying line as well as the net rate $dX_{rec}/dt$ with a downstream branch in the arterial line with respect to the venous line from the blood-carrying line at the same blood flow rate $Q_B$, and then from that determining the blood flow rate $Q_F$ according to the following equation:

$$Q_F = \frac{Z}{1-Z} Q_B \text{ where } Z = \frac{\frac{dX_{rec}}{dt}}{\frac{dX}{dt}} \frac{Y_V - Y_A}{Y_{V,rec} - Y_A}.$$

21. The device according to claim 10, characterized in that the arterial line and the venous line are part of an extracorporeal blood circulation system of a blood treatment device.

22. The device according to claim 21, wherein the blood treatment device is a hemodialysis device.

23. The device according to claim 21, wherein the blood flow rate $Q_F$ to be determined is the blood flow in a blood vessel, in a patient.

24. The device according to claim 10, wherein device has a display unit suitable for displaying the blood flow rate $Q_F$.

* * * * *

UNITED STATES PATENT AND TRADEMARK OFFICE
CERTIFICATE OF CORRECTION

PATENT NO. : 7,704,213 B2
APPLICATION NO. : 10/540110
DATED : April 27, 2010
INVENTOR(S) : Matthias Kraemer It is certified that error appears in the above-identified patent and that said Letters Patent is hereby corrected as shown below:

In the Specification

Column 1, line 20, delete "from".

In the Claims

Column 9, line 54, after "basis of the", insert --equation:--;

Column 10, line 53, change "$Q_F$" to --$Q_B$--;

Column 11, line 42, after "branch" insert --in--; and

Column 12, line 39, after "vessel", delete the ",".

Signed and Sealed this
Twenty-fourth Day of September, 2013

Teresa Stanek Rea
*Deputy Director of the United States Patent and Trademark Office*